United States Patent [19]

Hamas

[11] Patent Number: 4,531,244
[45] Date of Patent: Jul. 30, 1985

[54] MAMMARY PROSTHESIS WITH MULTIPLE FLOW SPACES

[76] Inventor: Robert S. Hamas, Woodhill Medical Park, 8345 Walnut Hill, Suite 120, Dallas, Tex. 75231

[21] Appl. No.: 513,754
[22] Filed: Jul. 14, 1983
[51] Int. Cl.³ .............................................. A61F 1/00
[52] U.S. Cl. .................................................... 623/8
[58] Field of Search ........................... 3/36, 1; 128/79; 206/814, 584

[56] References Cited

U.S. PATENT DOCUMENTS 3,366,975  2/1968  Paugman ................................. 3/36

Primary Examiner—Richard J. Apley
Assistant Examiner—James Prizant
Attorney, Agent, or Firm—Webb, Burden, Robinson & Webb

[57] ABSTRACT

A mammary prosthesis comprising an envelope of an inert elastomer for containing an inert fluid material. The envelope is composed of a plurality of firm protuberances distributed substantially equally thereover. These protuberances may be platelike, ridges, tubes, or posts. The protuberances may be in one or more layers and may be covered with an outer envelope of inert elastomer which may be perforated or in the form of a web. The protuberances provide therebetween flow spaces such that when the scar capsule contracts and compresses the protuberances, the mammary prosthesis will have a space for displacement and remain soft. The protuberances further provide greater localized pressure in pounds per square inch against the scar capsule for a given amount of massage exercise done after surgery. Since scar stretches in response to pressure, this reduces the amount of scar contracture of the capsule.

18 Claims, 6 Drawing Figures

MAMMARY PROSTHESIS WITH MULTIPLE FLOW SPACES

BACKGROUND

In my prior patent, U.S. Pat. No. 4,264,990, I explained the problems with prior art mammary prostheses and disclosed and claimed mammary prostheses that have a unique rigid back to prevent hardening by scar contracture. I have now invented another mammary prosthesis that will resist scar contracture and which will be easier to implant than those described in the above noted patent. In U.S. Pat. No. 3,366,975, a foamed coating over the surface of the mammary prosthesis is suggested to promote ingrowth of tissue and attachment of tissue to the surface of the prosthesis. According to the invention disclosed in this application, the surface of the prosthesis is provided with a plurality of rigid protuberances but in such a way to avoid tissue ingrowth and attachment. It should further be understood that this invention does not simply comprise providing a rough surface on the prosthesis but a pattern of projections especially arranged and spaced to hold the scar tissue from the surface of the implant envelope thus providing a space into which the envelope can be stretched. In this way, the implant can change shape even when the scar tissue has contracted.

SUMMARY OF THE INVENTION

Briefly, according to this invention, there is provided a mammary prosthesis with a soft envelope of an inert elastomer for being filled with an inert fluid material. A plurality of rigid protuberances of an inert material are distributed over the surface of the filled envelope serving to space the scar tissue that forms upon implantation from the surface of the filled envelope. The space provides a flow space into which the filled envelope may be displaced to permit the prosthesis to change shape even after scar contracture. According to a preferred embodiment of this invention, the rigid protuberances have a depth between one and ten millimeters and preferably between one and five millimeters. It is further preferred that the protuberances have a width at the base between one and ten millimeters and preferably between one and five millimeters. It is further preferred that the portion of the protuberances adjacent to the surface of the filled envelope is enlarged and fixed to the surface of the fitted envelope to maintain the protuberances substantially perpendicular to the surface of the filled envelope. The size and shape of the protuberances is such that they cannot be felt through the skin. In yet another embodiment, the protuberances are secured to the interior of one or more additional, but unfilled, envelopes of an inert elastomer positioned to surround the filled envelope with the ends of the protuberances bearing upon the envelope just inward thereof. In still yet another embodiment, the protuberances are secured at one end to the surface of the filled envelope and are interconnected near the distal ends thereof by a web of inert elastomer material serving to hold the protuberances substantially perpendicular to the surface. Preferably the web may support at least one more set of protuberances extending substantially perpendicular to the filled envelope surface and may have an unfilled envelope or web extending over the distal ends of the outermost set of protuberances to prevent tissue ingrowth.

THE DRAWINGS

Further features and other objects and advantages of this invention will become clear from the following detailed description made with reference to the drawings in which:

FIG. 1 is a front view of one embodiment according to this invention in which protuberances are disk-like;

DESCRIPTION OF THE PREFERRED EMBODIMENTS

According to this invention, there is provided a mammary prosthesis comprising a flexible envelope of an inert elastomer for being filled with an inert fluid material. It may be of the double or triple lumen type, for example, wherein the envelope has multiple enclosures therein. The flexible filled envelope has a plurality of firm protuberances spaced over the surface thereof. The protuberances may comprise firm ridges, tubes, knobs, or projections of various shapes including elongate, oval, square, round, star-shaped and so forth. The protuberances may be arranged in a variety of patterns and may be of various types. The protuberances preferably cover no more than fifty percent of the surface of the envelope in order to provide a flow space between the envelope and the scar tissue which forms thereover. This provides a space into which the elastic portions of the filled envelope may be displaced after the scar envelope has contracted against the protuberances.

Figure 1:
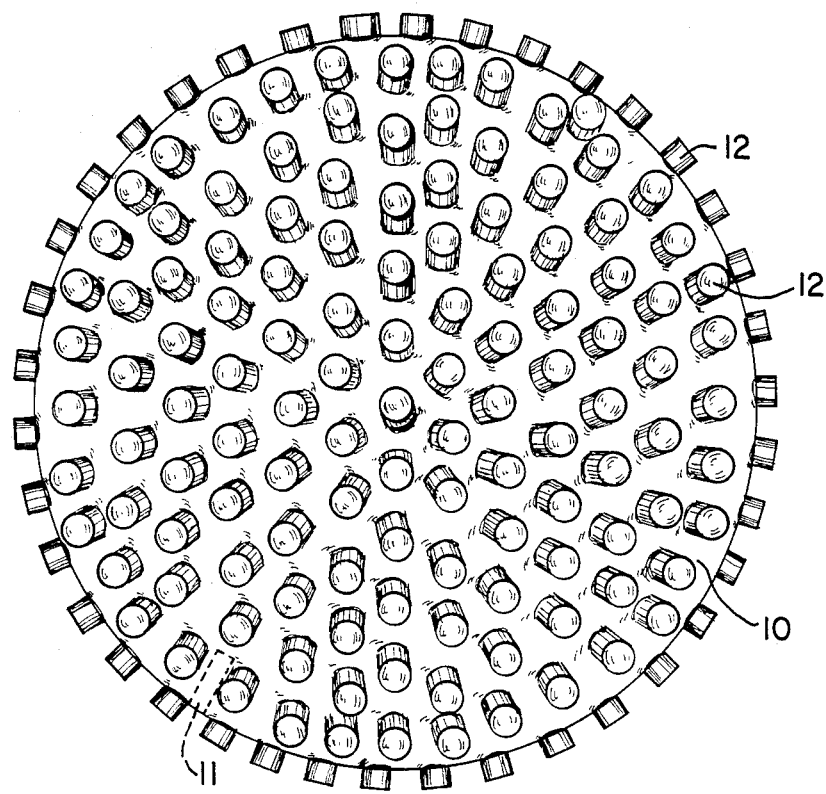
Figure 2:
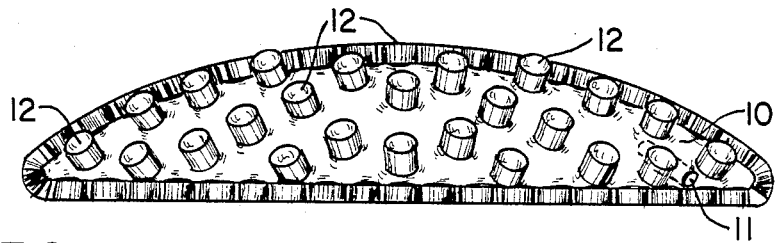
FIG. 2 is a side view of the same.

Referring now to FIGS. 1 and 2, there is shown a mammary prosthesis according to this invention comprising a filled envelope 10 which is a silicone elastomer or the like and which is either prefilled, for example with a silicone gel, or provided with a valve 11 such that it may be inflated after implacement with a saline solution or the like as is typical practice. Over the entire surface of the envelope are rigid platelets 12. The platelets are constructed of silicone plastic or like material which is biologically inert. The platelets may either be made of a more rigid material than the envelope and then fastened thereto or the platelets may be of the same material in which case rigidity is supplied by the additional thickness of the platelets. According to this embodiment, the protuberances have a width between one and five millimeters and a thickness between one and five millimeters.

Figure 3:
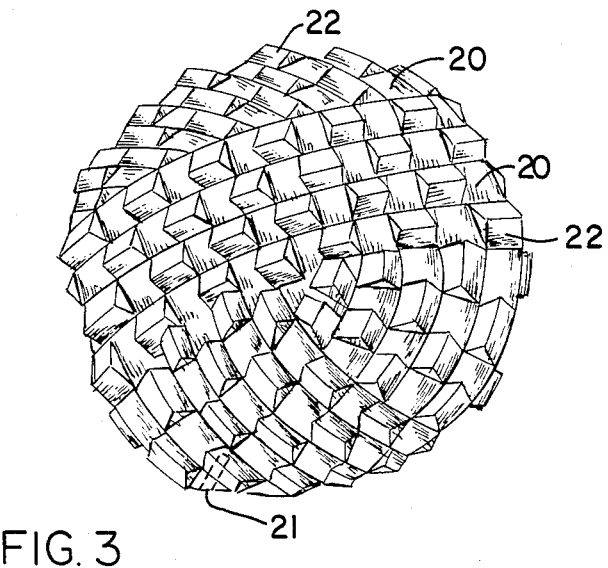
FIG. 3 is a front view of an alternate embodiment according to this invention in which the protuberances comprise ridges.

Referring now to FIG. 3, there is shown an alternate embodiment comprising a filled envelope 20 which is a silicone elastomer envelope or the like either prefilled or provided with a valve 21. Over the surface of the envelope are a plurality of rigid ridges 22. The ridges may be formed in the same manner suggested for the platelets described with reference to the embodiment of FIGS. 1 and 2.

Figure 4:
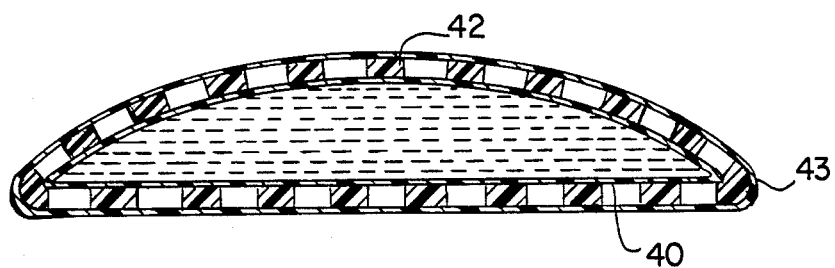
FIG. 4 is a side view in section of an alternate embodiment according to this invention in which the protuberances are secured to the inside of an envelope placed over an implant.

Referring now to FIG. 4, there is shown yet another embodiment of this invention in which the prosthesis comprises a filled envelope 40, a second unfilled envelope 43 having a plurality of protuberances 42 secured to extend inwardly of the unfilled envelope 43. The protuberances bear upon the surface of the filled envelope 40. The unfilled envelope 43 may be perforated to allow fluids to pass therethrough but to prevent cells from passing (millipore size perforations).

Figure 5:
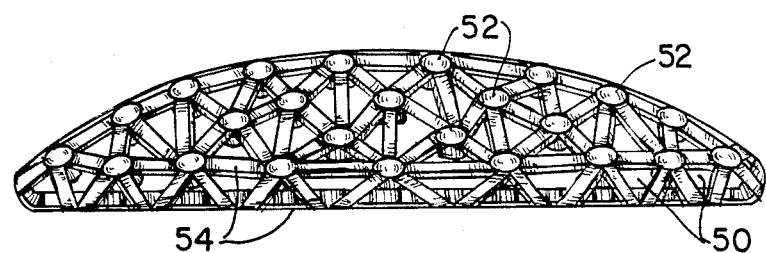
FIG. 5 is a side view of an embodiment according to this invention in which the protuberances are secured by an interconnecting web.

According to yet another embodiment of this invention as shown in FIG. 5, a filled envelope 50 has a plurality of protuberances 52 spaced over the surfaces thereof which are interconnected by webs 54 which help to maintain the erection of the protuberances perpendicular to the surface of the envelope 50.

Figure 6:
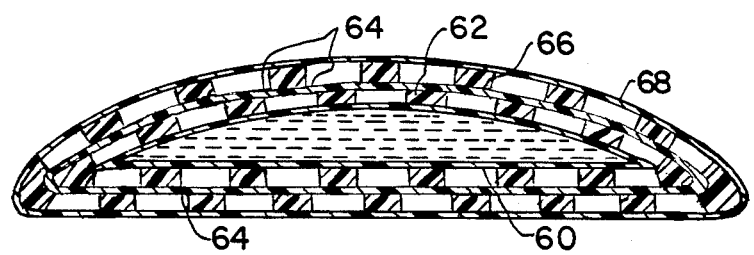
FIG. 6 is a side view in section, of an embodiment according to this invention in which there are multiple sets of protuberances supported by webs and covered by an envelope impervious to cellular or tissue ingrowth.

Referring now to FIG. 6, there is shown a modification of the embodiment shown in FIG. 5 wherein the filled envelope 60 has secured thereto a first set of protuberances 62 with interconnecting web 64 and a second set of protuberances 66 supported from the interconnecting web. (Additional sets of protuberances may be used.) There is an optional second envelope 68 enclosing the second set of protuberances 66.

The mammary prosthesis with firm protuberances will have outside dimensions as if there were no protuberances and the volume of the fluid were increased. For example, a 250 cc low profile, smooth wall mammary implant as is commercially available has a diameter of 124 millimeters and a thickness of 28 millimeters. The same space would be occupied by an implant that had four millimeter firm protuberances and a filled envelope with a diameter of about 116 millimeters and a thickness at 20 millimeters. The volume of the filled envelope would be proportionately less than 250 cc. When the scar capsule matures, it customarily undergoes some degree of contraction creating tension around the scar. This contracture brings the scar capsule into a position to rest upon the distal ends of the protuberances of the mammary prosthesis. The firm protuberances take up a small amount of the total volume, say one-quarter to one-half of the space between the envelope and the scar capsule. The remaining volume is empty space into which the contents of the prosthesis can flow. Since the prosthesis can be displaced into the flow space, it is more pliable and appears more natural and soft than if the same space was filled with a smooth wall implant.

The scar will continue to contract creating increased tension until it encounters increased resistance from the mammary prosthesis. This occurs after varying degrees of contracture in different patients. As long as the contracture of the scar capsule was not so severe that the firm protuberances were completely depressed into the substance of the mammary prosthesis there remains a flow space between the elastomer portion of the flexible envelope and the scar. This permits displacement of the inner contents of the mammary prosthesis between protuberances and makes the breast feel soft.

In an attempt to reduce the degree of contracture of the scar envelope around the mammary prosthesis, it is customary to massage the breast and mammary prosthesis after surgery. This is done several times per day for up to a year or longer while the scar is maturing. Scar tissues respond to pressure by aligning the collagen fibers and stretching. Patients apply pressure to the mammary prosthesis and the surrounding scar capsule. The presence of protuberances allows the patient to apply greater local pressure against the scar capsule than would be the case with the smooth walled implant. It is expected the scar capsule will respond to this increased pressure with further stretching to allow more volume into which the mammary prosthesis can be displaced.

Having thus defined the invention with the detail and particularity required by the Patent Laws, what is desired protected by Letters Patent is set forth in the following claims.

I claim:

1. A mammary prosthesis comprising a soft envelope of an inert elastomer for containing an inert fluid material, a plurality of rigid protuberances of an inert material distributed over the surface of the envelope, and having distal ends spaced from said surface a sufficient distance so as to space the scar tissue that forms upon implantation from the surface of the envelope providing a flow space therebetween into which the envelope may be displaced to permit the prosthesis to change shape.

2. A mammary prosthesis according to claim 1 in which the rigid protuberances have a depth between one and ten millimeters.

3. A mammary prosthesis according to claim 2 in which the rigid protuberances have a width between one and ten millimeters.

4. A mammary prosthesis according to claim 1 in which the portion of the protuberances adjacent the surface of the envelope is enlarged and fixed to the surface to maintain the protuberances substantially perpendicular to the surface of the envelope.

5. A mammary prosthesis according to claim 1 wherein the protuberances are secured extending inwardly of a second envelope of an inert elastomer positioned to surround the soft envelope with the ends of the protuberances bearing thereupon.

6. A mammary prosthesis according to claim 5 wherein the second envelope supports at least one more set of protuberances.

7. A mammary prosthesis according to claim 5 wherein the second envelope has porosity for only passing liquids.

8. A mammary prosthesis according to claim 1 wherein the protuberances are secured at one end to the surface of the soft envelope and are interconnected near the distal ends thereof by a web of inert elastomer material serving to hold the protuberances substantially perpendicular to the surface.

9. A mammary prosthesis according to claim 8 wherein the web supports at least one more set of protuberances extending substantially perpendicular to said envelope surface.

10. A mammary prosthesis according to claim 9 wherein a web or envelope extends between the distal ends of the outermost set of the protuberances.

11. A mammary prosthesis according to claim 1 wherein the protuberances are secured at one end to the surface of the soft envelope and are interconnected near the distal ends thereof by an envelope of inert elastomer material serving to hold the protuberances substantially perpendicular to the surface.

12. A mammary prosthesis according to claim 11 wherein the envelope supports at least one more set of protuberances extending substantially perpendicular to said envelope surface.

13. A mammary prosthesis according to claim 12 wherein an envelope extends over the distal ends of the outermost set of the protuberances.

14. A mammary prosthesis according to claim 3 wherein a second envelope extends over the distal ends of the protuberances.

15. A mammary prosthesis according to claim 1 wherein the protuberances have a depth of between one and five millimeters.

16. A mammary prosthesis according to claim 1 wherein the protuberances have a width of between one and five millimeters.

17. An envelope for use with mammary prostheses comprising an inert elastomer having a plurality of rigid protuberances of an inert material distributed over the surface of the envelope and extending inwardly thereof and having one opening enabling the envelope to be placed over a mammary prosthesis prior to the time of implant.

18. A web for use with mammary prostheses comprising an inert elastomer having a plurality of rigid protuberances of an inert material distributed over the surface of the web and extending inwardly thereof and having one opening enabling the web to be placed over a mammary prothesis prior to the time of implant.

* * * * *